United States Patent
Chang et al.

(10) Patent No.: US 10,156,658 B1
(45) Date of Patent: Dec. 18, 2018

(54) DETECTING A TRACER IN A HYDROCARBON RESERVOIR

(71) Applicant: Saudi Arabian Oil Company, Dhahran (SA)

(72) Inventors: Sehoon Chang, Cambridge, MA (US); Wei Wang, Quincy, MA (US); Shannon L. Eichmann, Somervile, MA (US)

(73) Assignee: Saudi Arabian Oil Company

( * ) Notice: Subject to any disclaimer, the term of this patent is extended or adjusted under 35 U.S.C. 154(b) by 0 days.

(21) Appl. No.: 15/615,501

(22) Filed: Jun. 6, 2017

(51) Int. Cl.
| | |
|---|---|
| *G01J 3/44* | (2006.01) |
| *G01V 15/00* | (2006.01) |
| *E21B 49/08* | (2006.01) |
| *E21B 47/10* | (2012.01) |
| *G01N 21/65* | (2006.01) |

(52) U.S. Cl.
CPC .......... *G01V 15/00* (2013.01); *E21B 47/1015* (2013.01); *E21B 49/08* (2013.01); *G01N 21/658* (2013.01)

(58) Field of Classification Search
CPC .... G01N 21/65; G01N 2021/65; G01N 21/64; G01J 3/44; G01J 3/02; G01V 15/00; E21B 49/00; E21B 47/10
See application file for complete search history.

(56) References Cited

U.S. PATENT DOCUMENTS

| | | |
|---|---|---|
| 6,590,647 B2 | 7/2003 | Stephenson |
| 7,588,827 B2 | 9/2009 | Nie et al. |
| 7,879,625 B1 | 2/2011 | Boss |
| 8,337,783 B2 | 12/2012 | Locascio et al. |
| 2008/0110253 A1 | 5/2008 | Stephenson et al. |
| 2008/0111064 A1 | 5/2008 | Andrews et al. |
| 2010/0224823 A1 | 9/2010 | Yin et al. |
| 2011/0207231 A1 | 8/2011 | Natan et al. |
| 2011/0260051 A1 | 10/2011 | Preudhomme et al. |
| 2011/0275061 A1 | 11/2011 | Weidemaier et al. |
| 2012/0257199 A1* | 10/2012 | Liu ................. G01N 21/658 356/301 |

(Continued)

FOREIGN PATENT DOCUMENTS

| | | |
|---|---|---|
| EP | 2040075 | 3/2009 |
| WO | WO2015058206 A1 | 4/2015 |
| WO | WO2016087397 A1 | 6/2016 |

OTHER PUBLICATIONS

Gao et al., "A Surface Functional Monomer-Directing Strategy for Highly Dense Imprinting of TNT at Surface of Silica Nanoparticles," Journal of American Chemical Society, vol. 129, No. 25, Jun. 2007; pp. 7859-7866.

(Continued)

*Primary Examiner* — Abdullahi Nur
(74) *Attorney, Agent, or Firm* — Fish & Richardson P.C.

(57) ABSTRACT

The present disclosure describes methods and systems for detecting a tracer in a hydrocarbon reservoir. One method includes injecting a tracer at a first location in a reservoir, wherein the tracer mixes with subsurface fluid in the reservoir; collecting fluid samples at a second location in the reservoir; mixing a magnetic surface-enhanced Raman scattering (SERS) particle with the fluid samples; applying a magnetic field to the mixed fluid samples; and analyzing the fluid samples to detect a presence of the tracer in the fluid samples.

19 Claims, 9 Drawing Sheets

(56) References Cited

U.S. PATENT DOCUMENTS

| | | |
|---|---|---|
| 2013/0084643 A1 | 4/2013 | Conunarieu et al. |
| 2014/0186939 A1 | 7/2014 | Peterman et al. |
| 2014/0360973 A1 | 12/2014 | Yin et al. |
| 2015/0038347 A1 | 2/2015 | Johnson et al. |

OTHER PUBLICATIONS

Hu et al., "Smart Liquid SERS Substrates based on Fe3O4/Au Nanoparticles with Reversibly Tunable Enhancement Factor for Practical Quantitative Detection," Scientific Report, vol. 4, No. 7204, Nov. 2014; pp. 1-10.

Nie et al., "Probing Single Molecules and Single Nanoparticles by Surface-Enhanced Raman Scattering," Science, vol. 275, No. 5303, Feb. 1997; pp. 1102-1106.

Stiles et al., "Surface-Enhanced Raman Spectroscopy," Annual Review of Analytical Chemistry, vol. 1, No. 1, Jul. 2008; pp. 601-626.

International PCT Communication (Invitation to Pay Additional Fees and, Where Applicable, Protest Fees), issued in International Application No. PCT/US2018/035024 dated Aug. 31, 2018, 13 pages.

* cited by examiner

DETECTING A TRACER IN A HYDROCARBON RESERVOIR

TECHNICAL FIELD

This disclosure relates to detecting tracers in a hydrocarbon reservoir.

BACKGROUND

In a hydrocarbon reservoir, subsurface fluid flow patterns can be analyzed to develop a geological model for the hydrocarbon reservoir. The model can be used to generate one or more parameters that are useful in reservoir resource management, including, for example, well to well connectivity, fluid allocation, fracture locations, swept volumes, and residual oil saturations.

SUMMARY

The present disclosure describes methods and systems for detecting tracers in a hydrocarbon reservoir. One method includes injecting a tracer at a first location in a reservoir, wherein the tracer mixes with subsurface fluid in the reservoir; collecting fluid samples at a second location in the reservoir; mixing a magnetic surface-enhanced Raman scattering (SERS) particle with the fluid samples; applying a magnetic field to the mixed fluid samples; and analyzing the fluid samples to detect a presence of the tracer in the fluid samples. Other implementations include corresponding systems and apparatuses. Other implementations of this aspect include corresponding systems and apparatuses configured to perform the actions of the methods.

The details of one or more implementations of the subject matter of this disclosure are set forth in the accompanying drawings and the subsequent description. Other features, aspects, and advantages of the subject matter will become apparent from the description, the drawings, and the claims.

DESCRIPTION OF DRAWINGS

Like reference numbers and designations in the various drawings indicate like elements.

DETAILED DESCRIPTION

This disclosure generally describes methods and systems for detecting tracers in a hydrocarbon reservoir. In some implementations, tracer studies can be used to collect data for the subsurface fluid flow analysis. In a tracer study, one or more tracers can be injected at an injection site of the reservoir. The tracer can mix with the fluid in the subsurface under the injection site. For example, the tracer can diffuse into the fluid or can mix with the fluid due to advection. After some time, fluid samples can be collected at a producing site for analysis. The propagation patterns of the tracers between the injecting site and the producing site can be used to determine the presence and location of flow barriers and fractures between the two sites in the reservoir. In some cases, multiple injection sites and multiple producing sites can be selected in a reservoir. Tracers can be injected in each of the multiple injection sites and fluid samples can be collected at each of the multiple producing sites to analyze the fluid pattern of the entire reservoir.

In some implementations, surface-enhanced Raman scattering (SERS) can be used as a detection technique to determine whether tracers have been collected at the producing sites. Raman spectroscopy can be used to measure inelastic scattering due to the interaction between incident monochromatic light and the induced molecular vibrations of samples. The results from these responses are used to determine material properties and the delineation of the presence of certain molecular species. The Raman signal may provide a weak signal; thus it may be difficult to detect tracers that are low in concentration. Surface-enhanced Raman scattering (SERS) can be used to enhance the Raman signal by an order of magnitude of $10^8$-$10^{15}$. The SERS method enhances the Raman response when molecules are placed on or near a roughened metal surface or metal nanostructure such as gold, platinum, silver, copper, or the like.

In some cases, magnetic functionality can be incorporated in SERS-active nanoparticles to further enhance the detection performance. By mixing tracers and specially designed SERS-active particles in the subsurface fluid and magnetically aggregating the SERS-active particles, the tracers are concentrated to a small area and interact with the SERS hotspots, and thus the Raman signal can be enhanced and detection performance can be enhanced.

Figure 1:
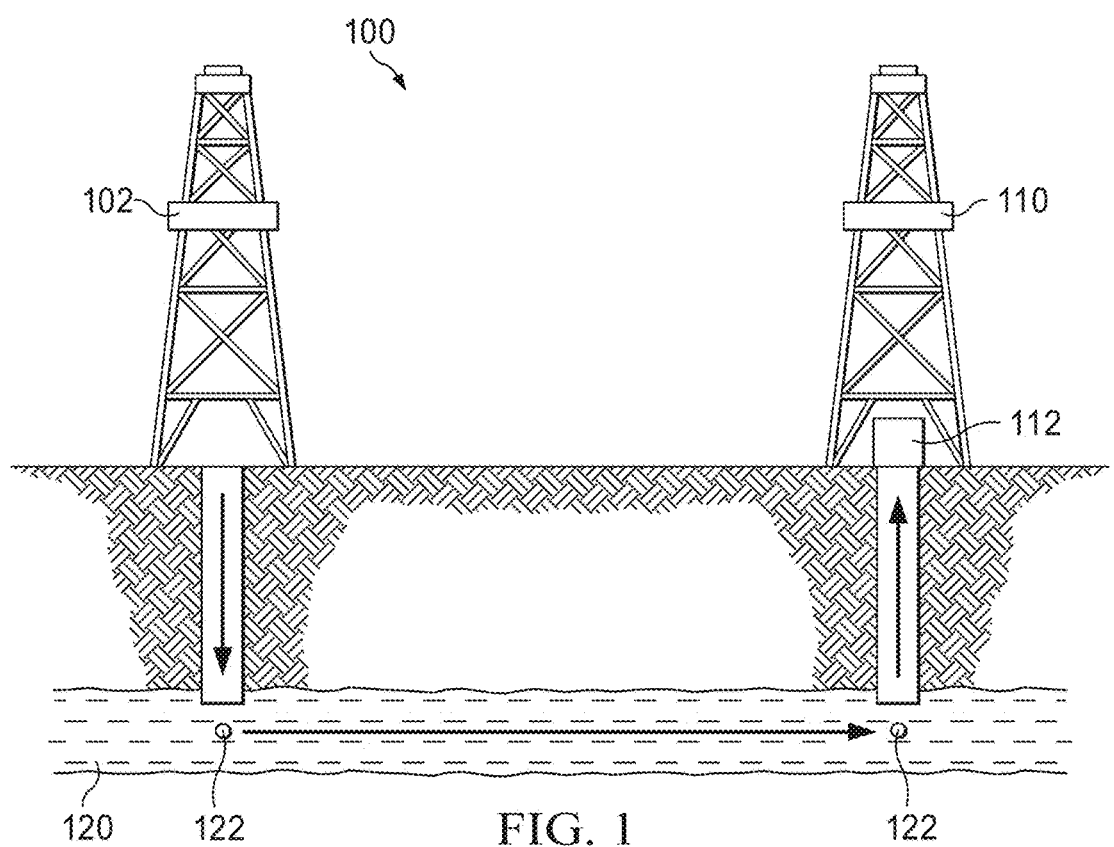
FIG. 1 is a schematic diagram that illustrates an example tracer detection system, according to an implementation.

FIG. 1 is a schematic diagram that illustrates an example tracer detection system 100, according to an implementation. The example tracer detection system 100 includes a first wellbore drilling system 102, located at an injection site. The first wellbore drilling system 102 can be implemented to inject one or more tracers 122 that can mix with subsurface fluid 120. The example tracer detection system 100 also includes a second wellbore drilling system 110 located at a producing site. The second wellbore drilling system 110 can be implemented to extract subsurface fluid 120 at the producing site. The example tracer detection system 100 also includes a tracer detection platform 112 located at the producing site.

A wellbore drilling system, for example, the first wellbore drilling system 102 and the second wellbore drilling system 110, can be implemented to inject fluids into a subsurface of a reservoir, extract fluids from the subsurface of the reservoir, or a combination thereof. For example, the first wellbore drilling system 102 can inject fluid into the subsurface using a wellbore at an injection site. The second wellbore drilling system 110 can extract subsurface fluid using a wellbore at a producing site.

The tracer detection platform 112 is a device that perform tracer detection of the fluids that are extracted at the producing site. In the illustrated example, the tracer detection platform 112 can be configured to perform magnetically enhanced SERS detections.

Figure 2:
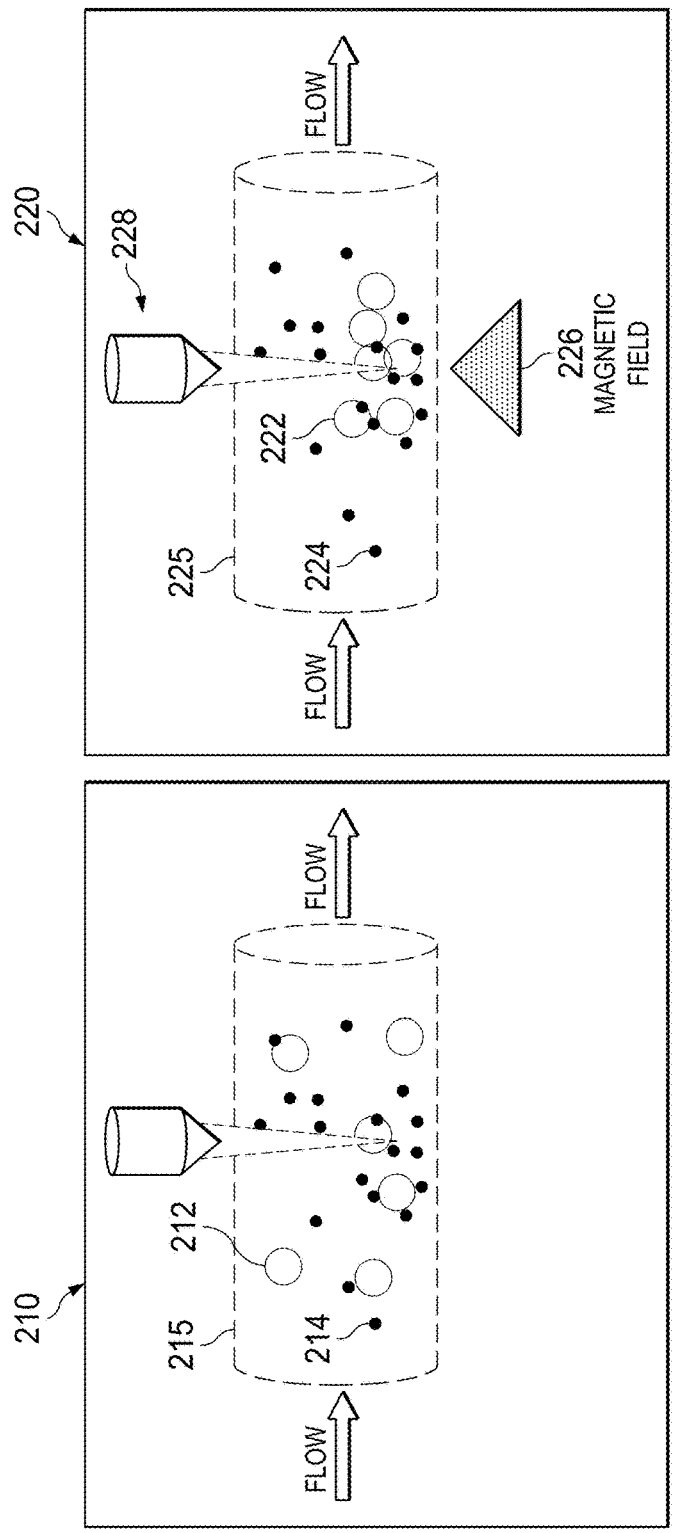
FIG. 2 illustrates a tracer detection platform before a magnetic field is applied and a tracer detection platform after the magnetic field is applied, according to an implementation.

FIG. 2 illustrates a tracer detection platform 210 before a magnetic field is applied and a tracer detection platform 220 after the magnetic field is applied, according to an implementation. In the platform 210, the subsurface fluid containing tracers 214 is extracted at the producing site and flows through a flow channel 215. The magnetic SERS nanoparticles 212 are mixed with the fluid. Without applying a magnetic field, the magnetic SERS nanoparticles 212 are distributed randomly in the fluid. Consequently, the metallic "hotspots" provided by the magnetic SERS nanoparticles 212 are also distributed randomly in the fluid.

In the platform 220, the subsurface fluid containing tracers 224 is extracted at the producing site and flows through a flow channel 225. At each detection time point, the magnetic SERS nanoparticles 222 are injected into the flow channel 225 and mixed with the fluid. A magnetic field 226 is applied. In some implementations, the magnetic field 226 can be generated using a neodymium permanent magnet, and the magnetic field 226 can be concentrated onto an attached needle tip which point to the sample chamber The activation of the magnetic field 226 causes the magnetic SERS nanoparticles 222 to concentrate into a detection region in the flow channel 225. Therefore, the tracers 224 interact with the metallic "hotspots" provided by the magnetic SERS nanoparticles 222 in the detection region. An optical source 228 generates an optical signal on the detection region to excite the SERS signals. The optical source 228 can be a laser device that generates a laser beam. In some implementations, the optical signal can be visible beams, for example, having wavelengths of 488 nm, 514 nm, 532 nm or 633 nm or near infrared (NIR) wavelengths at 785 nm or 1064 nm. The SERS signals can be detected to determine the presence of the tracers 224. At the end of detection window, the flow channel 225 is flushed and the fluid, including the tracers 224 and nanoparticles 222, is released into a waste collection stream. This process can be repeated for each measurement time point, thus providing a fresh set of SERS active particles for each measurement. The material consumption for the measurements is low because the amount of SERS-active particles injected for each measurement can be low.

The flow channel 225 is a conduit that is used to collect and separate produced fluids. In some cases, the flow channel 225 can be a microfluidic system. The microfluidic system provides simple sample collection, and magnetic force-induced nanoparticle migration. The microfluidic system can be a flow cell or chips with optical transparent window such as quartz. Once the superparamagnetic nanoparticles are injected or mixed into the fluid with the anlaytes, the magnet can be placed nearby the channel of the flow cell to collect nanoparticles. As shown in FIG. 2, a well-defined amount of superparamagnetic particles can be injected, mixed with analytes and captured in a localized area on the channel side wall (dosing) of the flow channel 225 near the tip of magnet. Furthermore, the captured superparamagnetic particles on the flow channel 225 can be released into the flow of the fluid which contains the analytes in a controlled manner either by increasing rate of the sample flow or reducing strength of magnetic field. The strength of magnetic field can be reduced by increasing distance between particles inflow cell and the magnet. This approach provides a better SERS signal acquisition from localized superparamagnetic nanoparticles in the focal area.

Returning to FIG. 1, the tracer 122 can be any analytes that are used in the hydrocarbon field for subsurface fluid flow analysis. In one example, the tracer 122 can be a 4-fluorobenzoic acid (FBA) analyte. Other examples of the tracer 122 include organic dyes such as fluorescein analyte and fluorescein isothiocyanate (FITC) analyte. The analytes can include liquid type chemicals, gas phase analytes in oil field, or a combination thereof.

Figure 3:
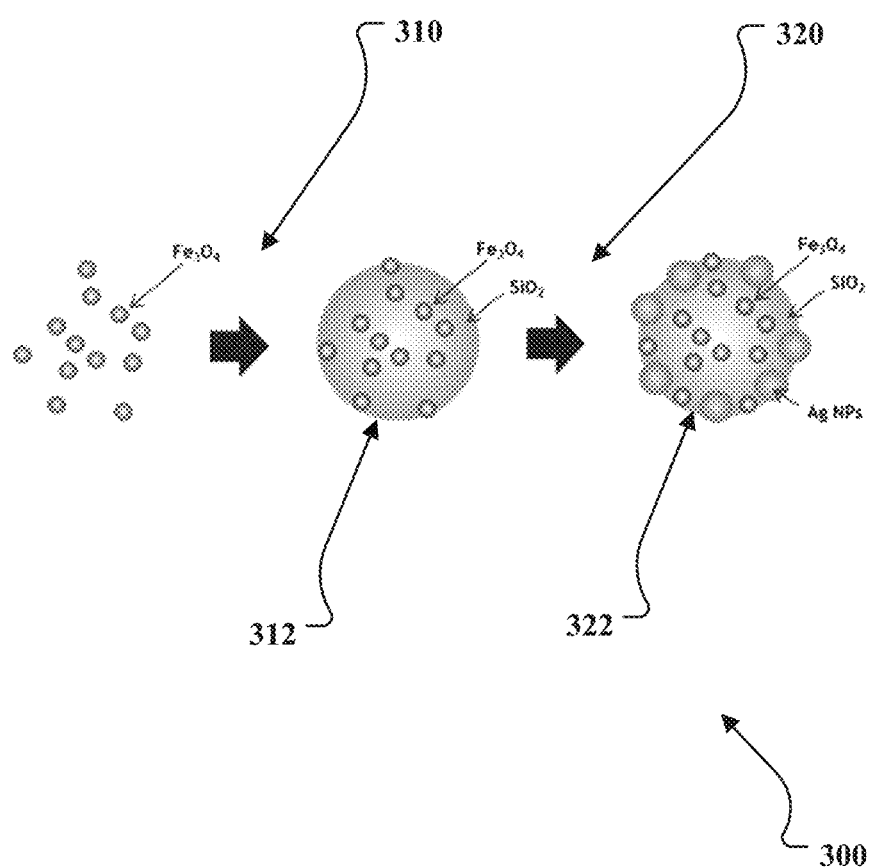
FIG. 3 is a schematic diagram that illustrates an example process for producing the SERS-active magnetic nanoparticles, according to an implementation.

FIG. 3 is a schematic diagram that illustrates an example process 300 for producing the SERS-active magnetic nanoparticles, according to an implementation. At step 310, the magnetic core particles, for example, $Fe_3O_4$, are incorporated into a non-magnetic particle shell, for example, $SiO_2$, to generate an incorporated particle 312. At step 320, the incorporated particle 312 is decorated with metallic particles, for example Ag or Au, to create SERS hotspots on the SERS-active magnetic nanoparticle 322. In some cases, the SERS-active magnetic nanoparticle 320 can also be decorated with other functionalizing materials to encourage the analyte materials to interact with the hotspots and improve SERS enhancement. In some cases, other magnetic materials can be used as the core seed particles, such as $\gamma\text{-}Fe_2O_3$, $MnFe_2O_4$, or $CoFe_2O_4$. In addition, other materials that are not Raman active can be used as shell, such as $TiO_2$ or $ZrO_2$.

Furthermore, the concentration and spacing of between the Ag particles can be adjusted to generate hotspots for optimizing SERS signal enhancement. The magnetic components ($Fe_3O_4$) and hotspot generators (Ag) can be also adjusted to produce the optimal collection efficiency and SERS signal enhancement. To improve the efficiency and the detection performance in the flow system, the adjustment of flow rate (for example lowering flow rate) and magnetic field (for example increasing magnetic field) during particle capture can be optimized by monitoring SERS signals from the controlled magnetic SERS nanoparticle aggregates with analytes.

Figure 4:
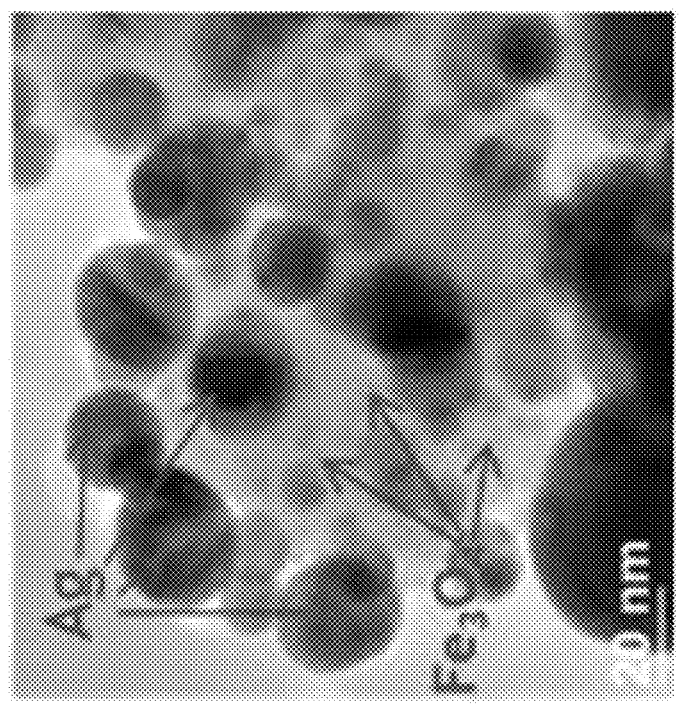
FIG. 4 is an example transmission electron microscopy (TEM) image of the SERS-active magnetic nanoparticle, according to an implementation

Following is an example procedure that can be used to produce one example batch of SERS-active magnetic nanoparticles. First, superparamagnetic colloidal $Fe_3O_4$ nanoparticles are synthesized by adding $FeCl_3.6H_2O$ (2.7 g) and $FeSO_4.7H_2O$ (1.39 g) in 100 ml of water with vigorous stirring. In some cases, $FeCl_2.4H_2O$ can be used instead of $FeCl_3.6H_2O$. Next, 10 ml of $NH_3.H_2O$ (29.5%) are added at 80° C. in a water bath for 20 minutes. After the formation of black superparamagnetic nanoparticles, the particles are drawn together using strong magnet and redispersed in deionized water several times to rinse. The superparamagnetic nanoparticles are then coated with $SiO_2$ ($Fe_3O_4@SiO_2$) by adding them to a microemulsion containing 27.5 g of IGEPAL CO-720 in 22.0 ml of hexanol plus 170 ml of cyclohexane. After vigorous stirring, 1 ml of (3-Aminopropyl) triethoxysilane and 0.25 mL of tetraethyl orthosilicate (TEOS) is added and stirred for 2 hrs. Next, 0.2 ml of (3-Mercaptopropyl) trimethoxysilane is added by stirring for 12 hours to finalize the $SiO_2$ coating. Ag nanoparticles are then attached to the $Fe_3O_4@SiO_2$ particles. Silver nanoparticles are synthesized by adding 0.002 M $AgNO_3$ (100 ml) into 0.01 M $NaBH_4$ (100 ml) and stirring for 3 hours. Ag nanoparticles are added into prepared $Fe_3O_4@SiO_2$ with volume ratios of 175:1 (Ag nanoparticle solution: $Fe_3O_4@SiO_2$ nanoparticles) and shaken (150 rpm) for 12 hours. FIG. 4 is an example transmission electron microscopy (TEM) image of the SERS-active magnetic nanoparticle, according to an implementation. These SERS-active magnetic nanoparticles can concentrate into a small region if a magnet is placed close to the solution containing the SERS-active magnetic nanoparticles.

Figure 5A:
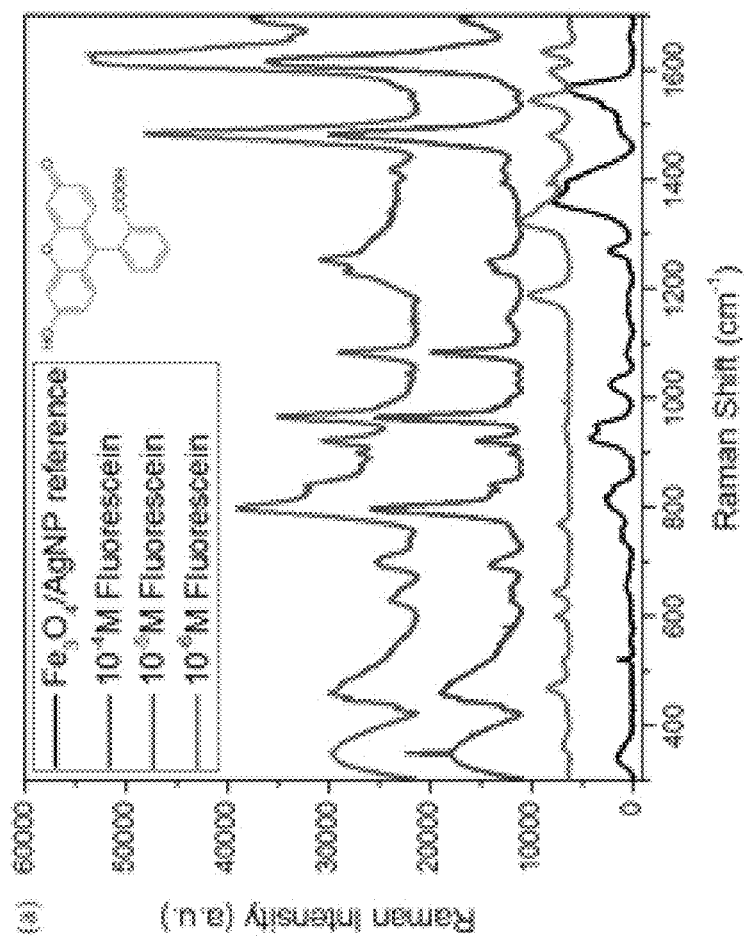
FIG. 5A-5C illustrates detection performances of the magnetically enhanced SERS detection, according to an implementation.
Figure 5B:
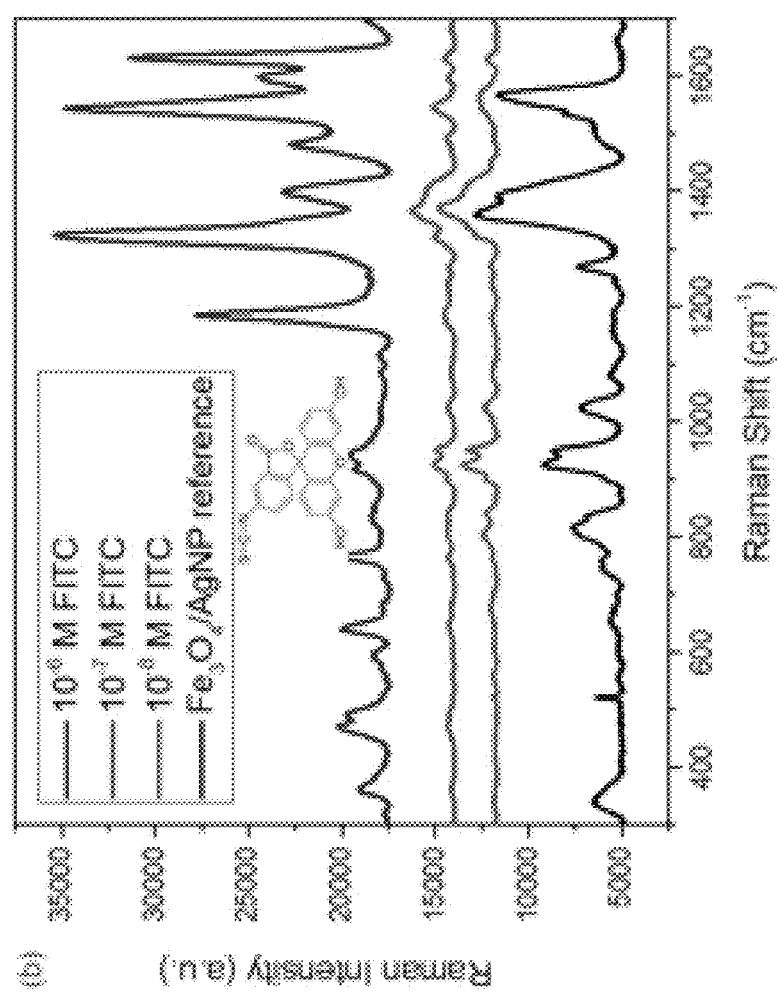
Figure 5C:
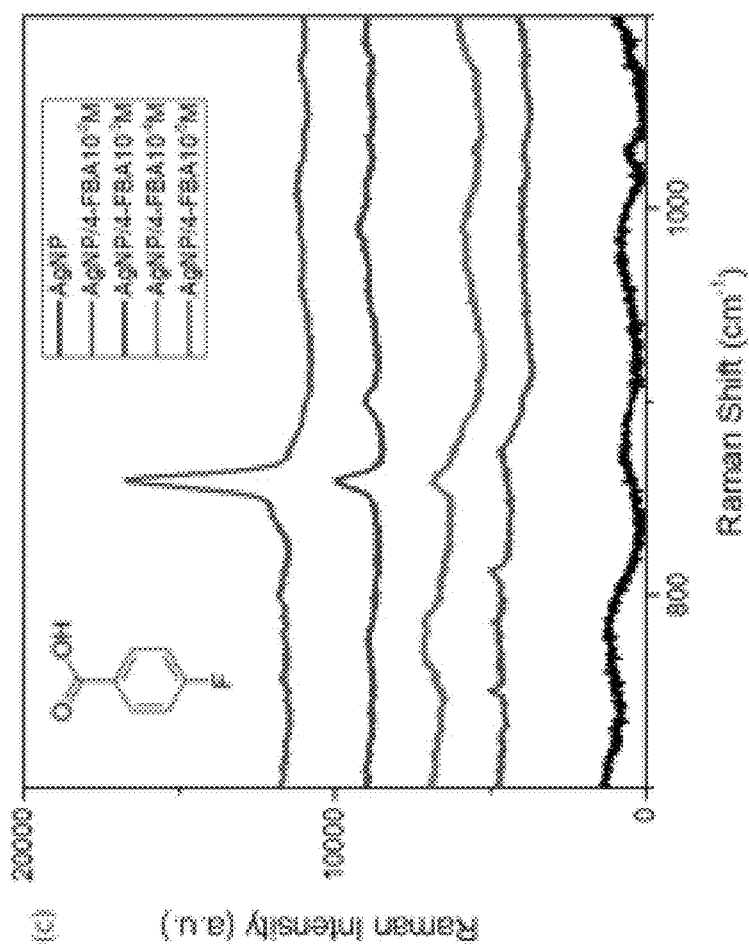

FIG. 5A-5C illustrate detection performances of the magnetically enhanced SERS detection, according to an implementation. These measurements are taken using a Raman spectrometer with an excitation of 532 nm and the limit of detection (LOD) can be determined by monitoring the characteristic peaks of the analyte molecule. Other wavelengths can be used for other analyte materials. FIG. 5A shows the detection performance of a solution of fluoresce analytes mixed with SERS-active magnetic nanoparticles. As shown in FIG. 5A, the limit of detection (LOD) can be determined at 10 μM for Fluorescein. FIG. 5B shows the detection performance of a solution of fluorescein isothiocyanate (FITC) analytes mixed with SERS-active magnetic nanoparticles. As shown in FIG. 5B, the limit of detection (LOD) can be determined at 10 nM for FITC. FIG. 5C shows the detection performance of a solution of 4-fluorobenzoic acid (FBA) analytes mixed with SERS-active magnetic nanoparticles. FBA is a material that is commonly used as tracers in oil fields. As shown in FIG. 5C, the limit of detection (LOD) can be determined at about 100 μM for FBA.

The LOD for FBA can be further improved by using specially selected particle coatings for specific tracer detection. For example, SERS nanoparticles can be selectively coated by acrylamide using charge-transfer interactions or polyelectrolytes using electrostatic interactions. This coating chemistry can be achieved by mixing of coating materials with SERS nanoparticles prior to the exposure to analyte molecules. Magnetic field can then be turned on for SERS measurement.

Figure 6:
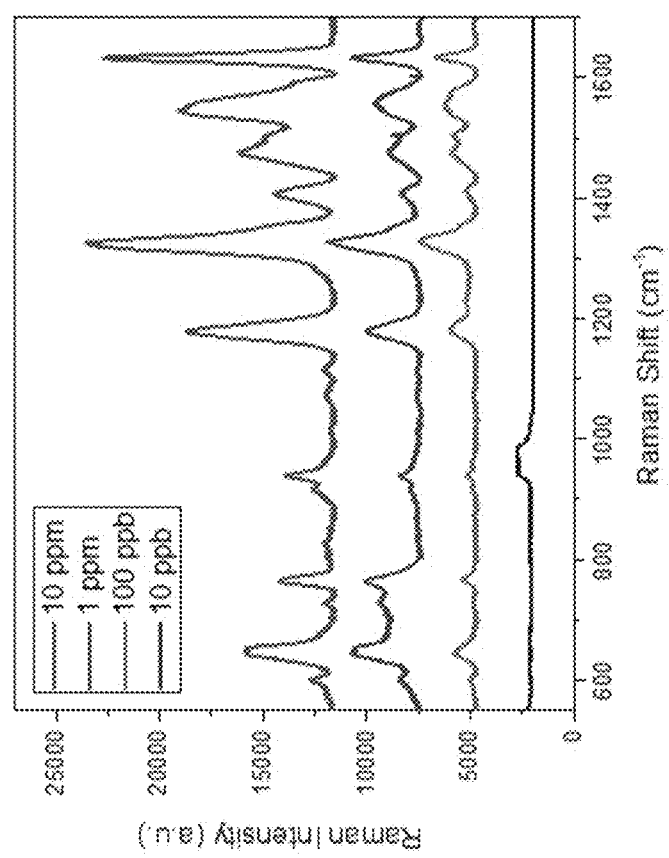
FIG. 6 illustrates detection performances using the magnetic SERS nanoparticles that are embedded with organic Raman markers, according to an implementation.

In some cases, organic Raman markers can be embedded into the magnetic SERS nanostructures. This approach can make the magnetic SERS nanoparticles into highly sensitive optical tracers. FIG. 6 illustrate detection performances using the magnetic SERS nanoparticles that are embedded with organic Raman markers according to an implementation. As shown in FIG. 6, the LOD can reach to 100 ppb level using embedded organic Raman markers. In addition, embedding different organic dyes, for example FITC, RBITC or thionine, that have specific Raman spectra into the magnetic SERS nanostructures can generate various bar-coded oil field tracers.

Figure 7:
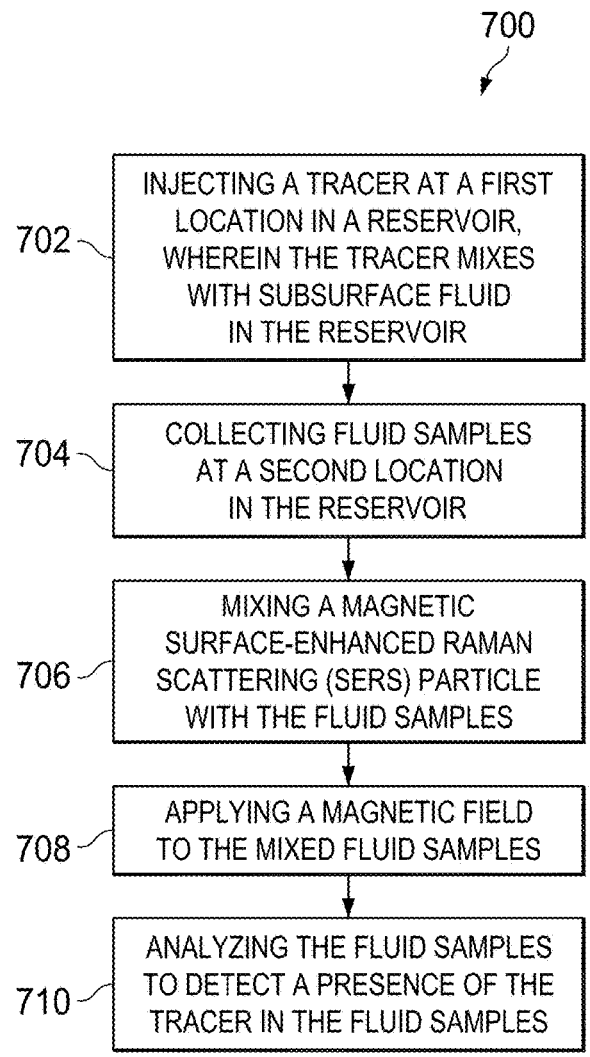
FIG. 7 is a flow diagram illustrating an example tracer detection process, according to an implementation.

FIG. 7 is a flow diagram illustrating an example tracer detection process 700, according to an implementation. The process 700 can be implemented using additional, fewer, or different steps, which can be performed in the order shown or in a different order. At 702, a tracer is injected at a first location in a reservoir. The tracer mixes with subsurface fluid in the reservoir. At 704, fluid samples are collected at a second location in the reservoir. At 706, a magnetic surface-enhanced Raman scattering (SERS) particle is mixed with the fluid samples. At 708, a magnetic field is applied to the mixed fluid samples. At 710, the fluid samples are analyzed to detect a presence of the tracer.

Described implementations of the subject matter can include one or more features, alone or in combination.

For example, in a first implementation, a method comprises: injecting a tracer at a first location in a reservoir, wherein the tracer mixes with subsurface fluid in the reservoir; collecting fluid samples at a second location in the reservoir; mixing a magnetic surface-enhanced Raman scattering (SERS) particle with the fluid samples; applying a magnetic field to the mixed fluid samples; and analyzing the fluid samples to detect a presence of the tracer in the fluid samples.

The foregoing and other described implementations can each, optionally, include one or more of the following features:

A first feature, combinable with any of the following features, wherein the magnetic SERS particle includes a magnetic core particle that is incorporated into a non-magnetic particle shell, the non-magnetic particle shell being decorated with metallic particles.

A second feature, combinable with any of the following features, wherein the magnetic core particle comprises at least one of an $Fe_3O_4$, $\gamma$-$Fe_2O_3$, $MnFe_2O_4$, or $CoFe_2O_4$ particle.

A third feature, combinable with any of the following features, wherein the metallic particles comprise at least one of an Ag or Au particle.

A fourth feature, combinable with any of the following features, wherein the non-magnetic particle shell comprises $SiO_2$.

A fifth feature, combinable with any of the following features, wherein the magnetic SERS particle is synthesized using $FeCl_3.6H_2O$ and $FeSO_4.7H_2O$.

A sixth feature, combinable with any of the following features, wherein the magnetic SERS particle is synthesized using $FeCl_2.4H_2O$ and $FeSO_4.7H_2O$.

A seventh feature, combinable with any of the following features, wherein the magnetic SERS particle is synthesized using microemulsion that contains IGEPAL CO-720 and cyclohexane.

An eighth feature, combinable with any of the following features, wherein the magnetic SERS particle is synthesized using triethoxysilane and tetraethyl orthosilicate (TEOS).

A ninth feature, combinable with any of the following features, wherein the magnetic SERS particle is synthesized by adding $AgNO_3$ into M $NaBH_4$.

A tenth feature, combinable with any of the following features, wherein the magnetic SERS particle is mixed with the fluid samples in a microfluidic system.

An eleventh feature, combinable with any of the following features, wherein the microfluidic system comprises a flow cell.

A twelfth feature, combinable with any of the following features, wherein the magnetic field is applied by placing a magnet near a channel of the flow cell.

A thirteenth feature, combinable with any of the following features, wherein the tracers are fluorobenzoic acids (FBAs) analytes.

A fourteenth feature, combinable with any of the following features, wherein the magnetic SERS particle is embedded with organic Raman markers.

In a second implementation, a magnetic surface-enhanced Raman scattering (SERS) particle comprises: a non-magnetic particle shell that is decorated with metallic particles, wherein the metallic particles comprise at least one of an Ag or Au particle; and a magnetic core particle that is incorporated into the non-magnetic particle shell, wherein the magnetic core particle comprises at least one of an $Fe_3O_4$, $\gamma$-$Fe_2O_3$, $MnFe_2O_4$, or $CoFe_2O_4$ particle.

The foregoing and other described implementations can each, optionally, include one or more of the following features:

A first feature, combinable with any of the following features, wherein the non-magnetic particle shell comprises $SiO_2$.

A second feature, combinable with any of the following features, wherein the magnetic SERS particle is synthesized using microemulsion that contains IGEPAL CO-720 and cyclohexane.

A third feature, combinable with any of the following features, wherein the magnetic SERS particle is synthesized using triethoxysilane and tetraethyl orthosilicate (TEOS).

A fourth feature, combinable with any of the following features, wherein the magnetic SERS particle is synthesized by adding $AgNO_3$ into $NaBH_4$.

This description is presented to enable any person skilled in the art to make and use the disclosed subject matter, and is provided in the context of one or more particular implementations. Various modifications to the disclosed implementations will be readily apparent to those skilled in the art, and the general principles defined herein may be applied to other implementations and applications without departing from scope of the disclosure. Thus, the present disclosure is not intended to be limited to the described and/or illustrated implementations, but is to be accorded the widest scope consistent with the principles and features disclosed herein.

Accordingly, the previous description of example implementations does not define or constrain this disclosure. Other changes, substitutions, and alterations are also possible without departing from the spirit and scope of this disclosure.

What is claimed is:

1. A method, comprising:
    injecting a tracer at a first location in a reservoir, wherein the tracer mixes with subsurface fluid in the reservoir;
    collecting fluid samples at a second location in the reservoir;
    mixing a magnetic surface-enhanced Raman scattering (SERS) particle with the fluid samples;
    applying a magnetic field to the mixed fluid samples; and
    analyzing the fluid samples to detect a presence of the tracer in the fluid samples.

2. The method of claim 1, wherein the magnetic SERS particle includes a magnetic core particle that is incorporated into a non-magnetic particle shell, the non-magnetic particle shell being decorated with metallic particles.

3. The method of claim 2, wherein the magnetic core particle comprises at least one of an $Fe_3O_4$, $\gamma$-$Fe_2O_3$, $MnFe_2O_4$, or $CoFe_2O_4$ particle.

4. The method of claim 2, wherein the metallic particles comprise at least one of an Ag or Au particle.

5. The method of claim 2, wherein the non-magnetic particle shell comprises $SiO_2$.

6. The method of claim 2, wherein the magnetic SERS particle is synthesized using $FeCl_3 \cdot 6H_2O$ and $FeSO_4 \cdot 7H_2O$.

7. The method of claim 2, wherein the magnetic SERS particle is synthesized using $FeCl_2 \cdot 4H_2O$ and $FeSO_4 \cdot 7H_2O$.

8. The method of claim 2, wherein the magnetic SERS particle is synthesized using microemulsion that contains IGEPAL CO-720 and cyclohexane.

9. The method of claim 2, wherein the magnetic SERS particle is synthesized using triethoxysilane and tetraethyl orthosilicate (TEOS).

10. The method of claim 2, wherein the magnetic SERS particle is synthesized by adding $AgNO_3$ into M $NaBH_4$.

11. The method of claim 2, wherein the magnetic SERS particle is mixed with the fluid samples in a microfluidic system.

12. The method of claim 11, wherein the microfluidic system comprises a flow cell.

13. The method of claim 12, wherein the magnetic field is applied by placing a magnet near a channel of the flow cell.

14. The method of claim 1, wherein the tracer is a fluorobenzoic acids (FBAs) analyte.

15. The method of claim 1, wherein the magnetic SERS particle is embedded with organic Raman markers.

16. A magnetic surface-enhanced Raman scattering (SERS) particle, comprising:
    a non-magnetic particle shell that is decorated with metallic particles, wherein the metallic particles comprise at least one of an Ag or Au particle;
    a magnetic core particle that is incorporated into the non-magnetic particle shell, wherein the magnetic core particle comprises at least one of an $Fe_3O_4$, $\gamma$-$Fe_2O_3$, $MnFe_2O_4$, or $CoFe_2O_4$ particle; and
    wherein the magnetic SERS particle is synthesized using microemulsion that contains IGEPAL CO-720 and cyclohexane.

17. The magnetic SERS particle of claim 16, wherein the non-magnetic particle shell comprises $SiO_2$.

18. The magnetic SERS particle of claim 16, wherein the magnetic SERS particle is synthesized by adding $AgNO_3$ into $NaBH_4$.

19. A magnetic surface-enhanced Raman scattering (SERS) particle, comprising:
    a non-magnetic particle shell that is decorated with metallic particles, wherein the metallic particles comprise at least one of an Ag or Au particle;
    a magnetic core particle that is incorporated into the non-magnetic particle shell, wherein the magnetic core particle comprises at least one of an $Fe_3O_4$, $\gamma$-$Fe_2O_3$, $MnFe_2O_4$, or $CoFe_2O_4$ particle; and
    wherein the magnetic SERS particle is synthesized using triethoxysilane and tetraethyl orthosilicate (TEOS).

* * * * *